(12) United States Patent
Gignac et al.

(10) Patent No.: US 7,105,817 B2
(45) Date of Patent: Sep. 12, 2006

(54) METHOD OF FORMING IMAGES IN A SCANNING ELECTRON MICROSCOPE

(75) Inventors: Lynne Gignac, Beacon, NY (US); Conal Murray, Yorktown Heights, NY (US); Oliver Wells, Yorktown Heights, NY (US)

(73) Assignee: International Business Machines Inc., Armonk, NY (US)

( * ) Notice: Subject to any disclaimer, the term of this patent is extended or adjusted under 35 U.S.C. 154(b) by 0 days.

(21) Appl. No.: 11/037,613

(22) Filed: Jan. 18, 2005

(65) Prior Publication Data

US 2006/0169894 A1    Aug. 3, 2006

(51) Int. Cl.
*G01N 23/00*    (2006.01)

(52) U.S. Cl. ............ 250/311; 250/306; 250/307; 250/396 R

(58) Field of Classification Search ............. None
See application file for complete search history.

(56) References Cited

U.S. PATENT DOCUMENTS

| | | | | |
|---|---|---|---|---|
| 5,592,563 A | * | 1/1997 | Zahavi | 382/154 |
| 6,844,550 B1 | * | 1/2005 | Yin et al. | 250/310 |
| 2005/0017173 A1 | * | 1/2005 | Kumar | 250/306 |

* cited by examiner

*Primary Examiner*—John R. Lee
*Assistant Examiner*—Zia R. Hashmi
(74) *Attorney, Agent, or Firm*—Rodney T. Hodgson

(57) ABSTRACT

An imaging device having many detector elements is used to construct multiple images of the surface of a specimen in a scanning electron microscope (SEM) using signals from different elements of the imaging device as the specimen is scanned a single time in the SEM.

16 Claims, 3 Drawing Sheets

METHOD OF FORMING IMAGES IN A SCANNING ELECTRON MICROSCOPE

FIELD OF THE INVENTION

The field of the invention is the field of scanning electron beam microscopes

BACKGROUND OF THE INVENTION

In a scanning electron microscope (SEM), a focused electron beam is scanned across the surface of a specimen. Electrons emitted from the region of the surface struck by the electron beam are detected, typically by a solid state diode or by a scintillator or phosphor that is optically coupled to a photomultiplier, and the current generated by the detected electrons determines the current of a beam of electrons in a cathode ray tube (CRT). As the focused electron beam is scanned over the surface, an image is built up on the CRT. SEM's are well known in the art and well described, for example, in numerous publications, starting with D. McMullan entitled "An improved scanning electron microscope for opaque specimens." published in Proc. IEE vol. 100 Pt. 11, 245–259 (1953).

The faster electrons are called backscattered electrons (BSE) and the image formed is called a BSE image.

OBJECT OF THE INVENTION

It is an object of the invention to produce a method of simultaneously recording scanning electron microscope images of an area of a surface.

DETAILED DESCRIPTION OF THE INVENTION

The image contrasts that are shown in a BSE image in the SEM will depend on the tilt angle of the specimen, the incident beam energy, the energy sensitivity of the BSE detector, the position of the BSE detector relative to the sample and the incident electron beam and other factors.

Figure 1:
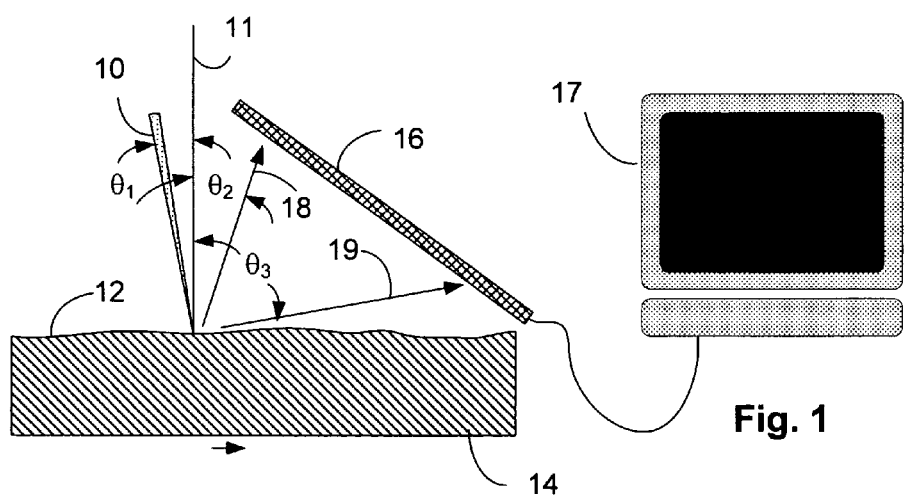
FIG. 1 shows a sketch of the apparatus of the invention.

The apparatus of the invention is shown in FIG. 1. A focused electron beam 10 is shown incident on a surface 12 of a specimen 14. Electron beam 10 forms an angle 0, with respect to the average normal to the surface 11. Electrons 18 and 19 are shown leaving the point of intersection of the electron beam 10 and the surface 12 with angles $\theta_2$ and $\theta_3$ with respect to the normal 11 respectively. The electron imaging device 16 required for the method of the invention is shown in side elevation intercepting electrons 18 and 19. Images constructed from signals from imaging device 16 are displayed on display device 17.

Figure 2:
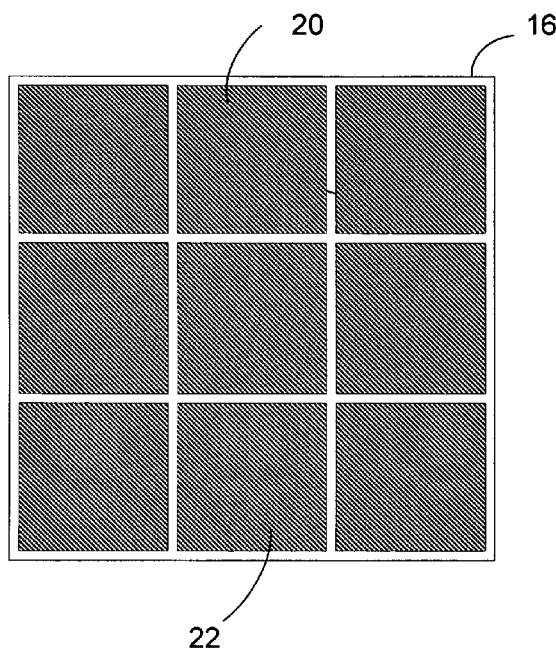
FIG. 2 shows a sketch of an imaging device of the invention.
Figure 3:
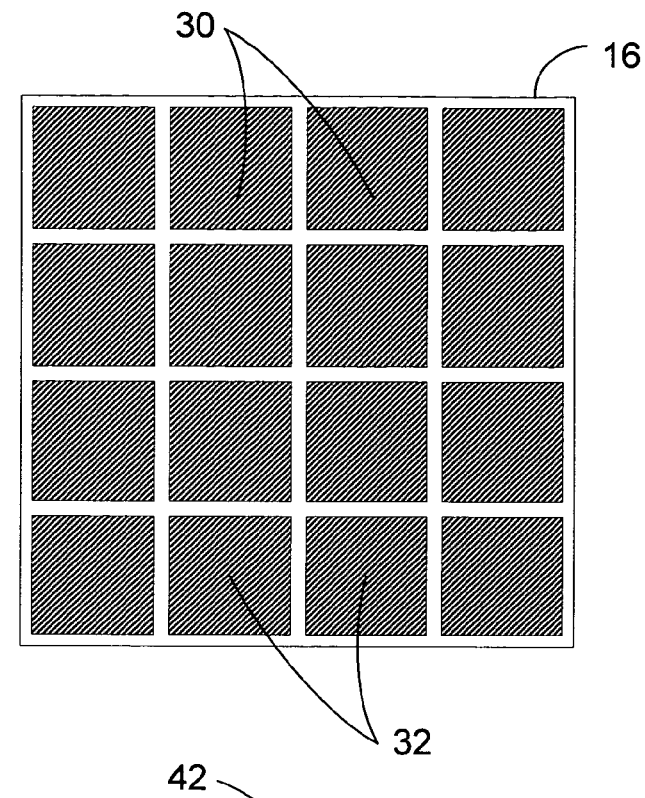
FIG. 3 shows a sketch of an imaging device of the invention.
Figure 4:
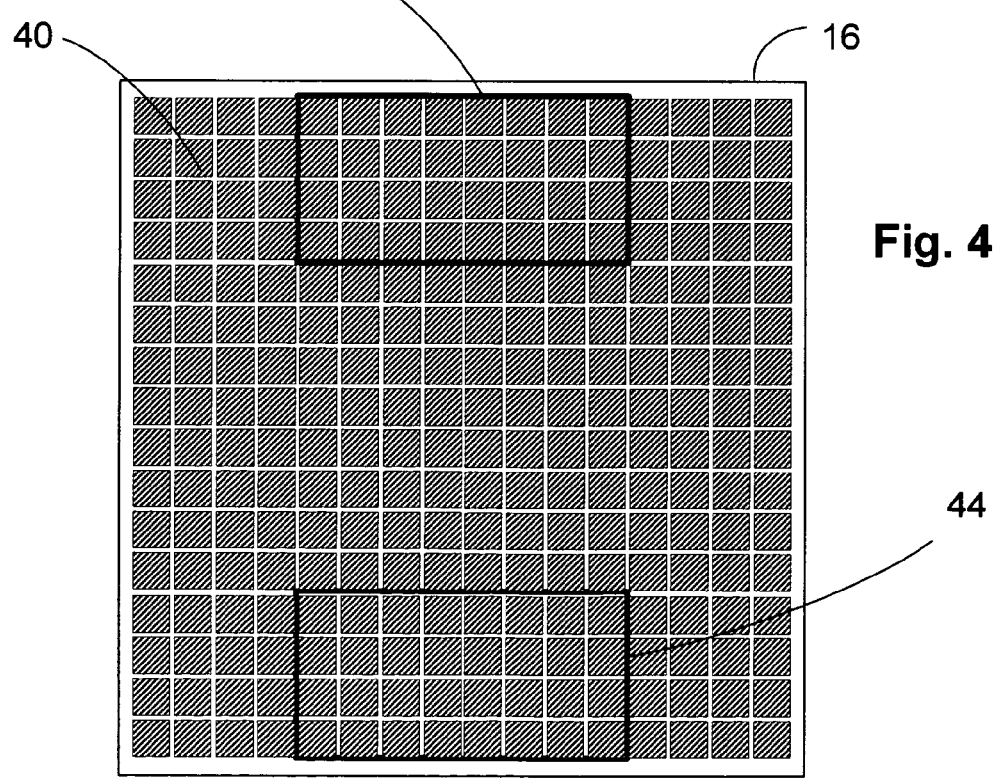
FIG. 4 shows a sketch of an imaging device of the invention.

Electron imaging devices 16 required for the method of the invention are shown in plan view in FIGS. 2, 3, and 4. The electron imaging device has a large plurality of individual detector elements, preferably 9 individual detector elements such as elements 20 and 22 as shown in FIG. 2, more preferably 16 individual elements such as elements 30 and 32 shown in FIG. 3, and most preferably at least 256 elements 40 as shown in FIG. 4. For the purposes of this specification, a large plurality of individual detector elements is defined as 9 elements or greater. Electron imaging devices of 1024 elements and up to millions of individual elements are currently available. The signals from a number of individual detector elements may be binned together in regions such as regions 42 and 44 of FIG. 4 to give a greater signal. The signals from such individual detector elements or combinations of elements may be used to construct and display an image of the surface on a display device as the electron beam 10 is scanned over the surface, or to construct and display a plurality of images of the surface.

The method of the invention comprises:
a) scanning an area of a surface of a specimen with an electron beam from a scanning electron microscope; then
b) detecting electrons scattered from the area of the surface of the specimen with an electron imaging device, the electron imaging device having a large plurality of individual detector elements; then
c) combining signals from at least a first individual detector element of the large plurality of individual detector elements to form a first image of the area of the surface of the specimen; and
d) combining signals from at least a second individual detector element of the large plurality of individual detector elements to form a second image of the area of the surface of the specimen;
wherein the signals from the at least first individual detector element and the at least second individual detector element of the large plurality of individual detector elements are recorded simultaneously in a single scan of the electron beam over the area of the specimen.

The method of the invention requires that at least two images are acquired as the electron beam 10 scans across the surface 12 of the specimen 14. For example, detector element 20 intercepts electrons which have a small angle $\theta_2$ with respect to the normal 11, and detector element 22 intercepts electrons which have a large angle $\theta_3$ with respect to the normal 11. The signal from each of the detector elements 20 and 22 is used to built separate images of the surface 12.

Figure 5:
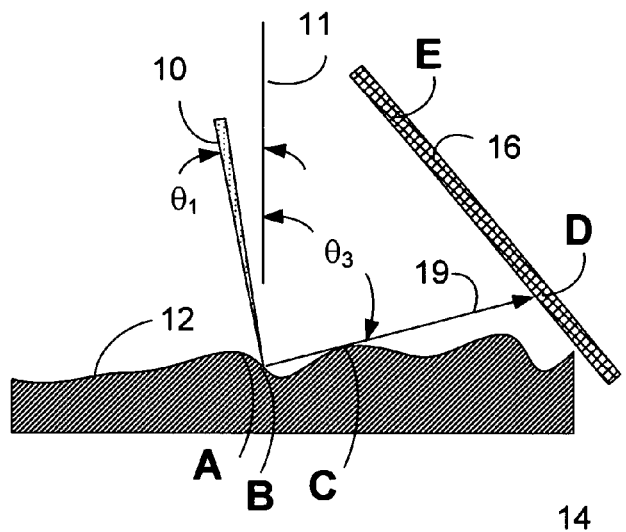
FIG. 5 shows a sketch of the apparatus of the invention.

Strong topographic contrasts can be obtained when using a BSE detector with a low takeoff angle, or a large angle $\theta_3$ with respect to the normal 11. FIG. 5 shows that the electron beam scanning from position A to B on the surface 12 will produce signal at positon D on device 16, in contrast to no signal when the beam scans from B to C. Thus, a detector at D will "see" a shadow as the beam scans from A to B. A detector located at position E on the device 16 will not see the shadow. As the takeoff angle is raised the topographic contrasts fade away to be replaced with magnetic contrast caused by the difference in composition, in magnetization between the magnetic domains, or in other differences in the material of the surface.

In the prior art, the collection solid angle of the BSE detector is changed by physically moving either a single detector or by the use of more than one detector. With the apparatus and method of the invention, however, the signals from the various regions of device 16 may be combined together to give images which emphasize features of importance, and the images may all be taken in the same scan of the electron beam over the surface 12 of the specimen. The ability to choose exactly which of the large plurality of detectors to use, or which combination of detectors, allows much more freedom to maximize signals, or emphasize features, than the prior art methods of SEM investigation. In addition, all the signals from all the detector elements may be recorded digitally or in analogue form, and images from a single scan of the surface can be reconstructed at a later time to construct the best images for the requirements.

Prior art BSE detectors having large pluralities of detector elements have been developed to record electron backscattering patterns (EBSP) from a single-crystal region of the sample as shown by L. Reimer entitled: "Scanning Electron Microscopy, Physics of Image Formation and Microanalysis." published by Springer-Verlag (Springer Series in Optical Sciences vol. 45) (1985) pp 338–341 and 356–361. Reimer points out that the probability of a Rutherford wide-angle scattering event at an atom in a single crystal is modulated by the incoming and outgoing channeling conditions and this gives rise to both the electron channeling pattern (ECP) for a rocking incident electron beam (EB); and to the EBSP in the emerging scattered electrons with a stationary incident EB. These are related by the reciprocity principle. EBSP are typically recorded using an array of very small BSE detectors that correspond to the pixels in the recorded pattern. The image recorded on the multielement BSE detector is a series of lines, called Kikuchi patterns, corresponding to the electrons which escape the crystal in channels. The surface of the specimen is not, however, imaged in this prior art.

Images of a polycrystalline surfaces showing poly crystalline contrast have been derived from a large number of such images of Kikuchi lines. These images, however, result from very computer intensive pattern recognition of the Kikuchi pattern orientation, and the time taken to record such an image is greater than the recording of images from the partitioned detectors of the present invention.

Figure 6:
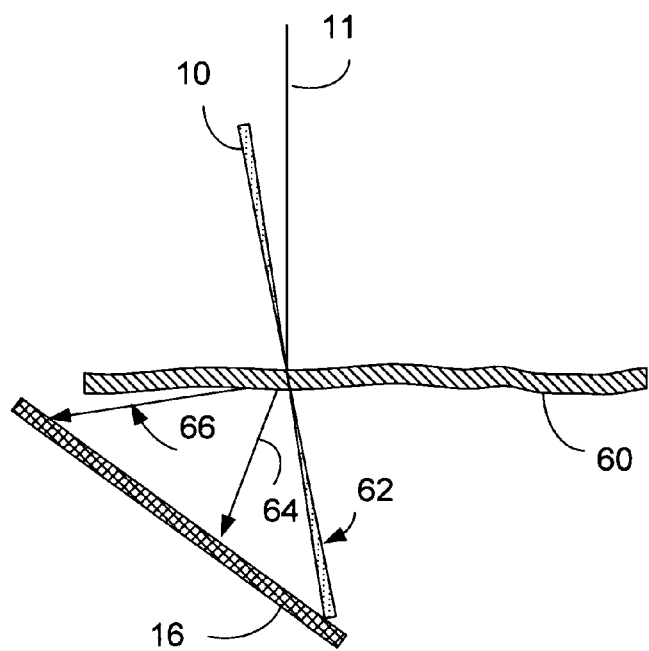
FIG. 6 shows a sketch of the apparatus of the invention.

In the case of a transmission electron image from a typically thinned specimen, the imaging device of the invention 16 is mounted below the specimen 60 as is shown in FIG. 6. This arrangement is typically referred to as a scanning transmission electron microscope (STEM). Once again, the collector solid angle has a very significant effect on the recorded image, and is typically referred to either as the bright-field collector solid angle (into which the incident electrons 62 will proceed if the specimen is removed from the microscope); or as the dark-field collector solid angle (which is just outside the bright field collector solid angle and which electrons 64 scattered at a small angle with respect to the incident electron beam 10 fall); or as the wide-angle dark-field collector solid angle (which can only be reached by electrons 66 that experience a larger deflection in the specimen). Once again, each of these collector solid angles may be subdivided and detected by the method of the invention, and multiple images may be obtained from a single scan of the specimen 60.

Obviously, many modifications and variations of the present invention are possible in light of the above teachings. It is therefore to be understood that, within the scope of the appended claims, the invention may be practiced otherwise than as specifically described.

We claim:

1. A method, comprising:
   a) scanning an area of a surface of a specimen with an electron beam from a scanning electron microscope; then
   b) detecting electrons scattered from the area of the surface of the specimen with an electron imaging device, the electron imaging device having a large plurality of individual detector elements; then
   c) combining signals from at least a first individual detector element of the large plurality of individual detector elements to form a first image of the area of the surface of the specimen; and
   d) combining signals from at least a second individual detector element of the large plurality of individual detector elements to form a second image of the area of the surface of the specimen;
   wherein the signals from the at least first individual detector element and the at least second individual detector element of the large plurality of individual detector elements are recorded simultaneously in a single scan of the electron beam over the area of the specimen.

2. The method of claim 1, wherein the electron imaging device has at least nine individual detector elements.

3. The method of claim 2, wherein the electron imaging device has at least 256 individual detector elements.

4. The method of claim 3, wherein the electron imaging device has at least 1024 individual detector elements.

5. The method of claim 4, wherein signals from individual detector elements are binned, and the binned signals are used to construct at least one image.

6. The method of claim 1 wherein at least one of the first or second images is displayed on a display device as the signals are recorded.

7. The method of claim 6, wherein at least both the first and the second images are displayed on a display device as the signals are recorded.

8. The method of claim 1, wherein electrons scattered from the surface having a relatively small angle with respect to the normal to the surface are detected to form the first image, and wherein electrons scattered from the surface having a relatively large angle with respect to the normal to the surface are detected to form the second image.

9. A method, comprising:
   a) scanning an area of a surface of a specimen with a single electron beam from a scanning electron microscope; then
   b) detecting electrons scattered from the area of the surface of the specimen with an electron imaging device, the electron imaging device having a large plurality of individual detector elements, wherein the electrons scattered are generated by the single electron beam; then
   c) combining signals from at least a first individual detector element of the large plurality of individual detector elements to form a first image of the area of the surface of the specimen; and
   d) combining signals from at least a second individual detector element of the large plurality of individual detector elements to form a second image of the area of the surface of the specimen;
   wherein the signals from the at least first individual detector element and the at least second individual detector element of the large plurality of individual detector elements are recorded simultaneously in a single scan of the electron beam over the area of the specimen.

10. The method of claim 1, wherein the electron imaging device has at least nine individual detector elements.

11. The method of claim 2, wherein the electron imaging device has at least 256 individual detector elements.

12. The method of claim 3, wherein the electron imaging device has at least 1024 individual detector elements.

13. The method of claim 4, wherein signals from individual detector elements are binned, and the binned signals are used to construct at least one image.

14. The method of claim 1, wherein at least one of the first or second images is displayed on a display device as the signals are recorded.

15. The method of claim 6, wherein at least both the first and the second images are displayed on a display device as the signals are recorded.

16. The method of claim 1, wherein electrons scattered from the surface having a relatively small angle with respect to the normal to the surface are detected to form the first image, and wherein electrons scattered from the surface having a relatively large angle with respect to the normal to the surface are detected to form the second image.

* * * * *